United States Patent
Halas et al.

(10) Patent No.: US 11,504,437 B2
(45) Date of Patent: Nov. 22, 2022

(54) MULTIFUNCTIONAL FLUORESCENT AND MRI-ACTIVE NANOSTRUCTURE

(71) Applicant: William Marsh Rice University, Houston, TX (US)

(72) Inventors: Nancy J. Halas, Houston, TX (US); Ciceron Ayala-Orozco, Stafford, TX (US); Sandra Bishnoi, Houston, TX (US); Luke Henderson, Houston, TX (US); Oara Neumann, Houston, TX (US); Robia Pautler, Houston, TX (US); Peter Nordlander, Houston, TX (US)

(73) Assignees: WILLIAM MARSH RICE UNIVERSITY, Houston, TX (US); BAYLOR COLLEGE OF MEDICINE, Houston, TX (US)

( * ) Notice: Subject to any disclaimer, the term of this patent is extended or adjusted under 35 U.S.C. 154(b) by 327 days.

(21) Appl. No.: 15/706,429

(22) Filed: Sep. 15, 2017

(65) Prior Publication Data
US 2018/0008730 A1 Jan. 11, 2018

Related U.S. Application Data

(63) Continuation-in-part of application No. 14/823,891, filed on Aug. 11, 2015, now abandoned.
(Continued)

(51) Int. Cl.
*A61K 49/18* (2006.01)
*H01B 3/02* (2006.01)
(Continued)

(52) U.S. Cl.
CPC ...... *A61K 49/1881* (2013.01); *A61K 49/1833* (2013.01); *C23C 18/1646* (2013.01); *C23C 18/31* (2013.01); *H01B 3/02* (2013.01)

(58) Field of Classification Search
None
See application file for complete search history.

(56) References Cited

U.S. PATENT DOCUMENTS

2008/0003184 A1* 1/2008 Uvdal ............... B82Y 5/00
424/9.32
2010/0254911 A1* 10/2010 Sharma ............ A61K 49/0093
424/9.32
(Continued)

FOREIGN PATENT DOCUMENTS

WO WO-2014036470 A1 * 3/2014 ......... A61K 49/1881
WO WO-2015054493 A1 * 4/2015 ............. B22F 1/0025

OTHER PUBLICATIONS

Hu, Y., et al., "Optical properties of gold-silica-gold multilayer nanoshells" Optics Express, pp. 19579-19591 (Year: 2008).*
(Continued)

*Primary Examiner* — Isaac Shomer
(74) *Attorney, Agent, or Firm* — Osha Bergman Watanabe & Burton LLP

(57) ABSTRACT

A Magnetic Resonance Imaging (MRI) enhancement agent includes a plurality of particles, each particle including: a metal core; a dielectric shell disposed on the metal core comprising at least one MRI contrast agent; and a metal shell disposed on the exterior surface of the dielectric shell that encapsulates the dielectric shell.

18 Claims, 8 Drawing Sheets

Related U.S. Application Data

(60) Provisional application No. 62/395,188, filed on Sep. 15, 2016, provisional application No. 62/035,716, filed on Aug. 11, 2014.

(51) Int. Cl.
*C23C 18/16* (2006.01)
*C23C 18/31* (2006.01)

(56) References Cited

U.S. PATENT DOCUMENTS

| | | | | |
|---|---|---|---|---|
| 2011/0158915 A1* | 6/2011 | Bardhan | ............ | A61K 49/1878 424/9.32 |
| 2012/0128583 A1* | 5/2012 | Kim | ................... | A61K 49/105 424/1.37 |
| 2012/0212733 A1* | 8/2012 | Kodali | ................ | C09B 67/0097 356/301 |
| 2015/0250902 A1* | 9/2015 | Boyes | ................ | A61K 49/1878 424/9.323 |
| 2015/0258218 A1* | 9/2015 | Kircher | .............. | A61K 51/1251 424/1.29 |
| 2016/0250612 A1* | 9/2016 | Oldenburg | .......... | C09B 67/0007 428/404 |

OTHER PUBLICATIONS

Millipore-Sigma, "3,3'-Diethylthiatricarbocyanine iodide" accessed from: https://www.sigmaaldrich.com/catalog/product/aldrich/381306?lang=en&region=US; accessed on Mar. 3, 2020, pp. 1-4 (Year: 2020).*

Hu, K., et al., "Fabrication of Gd2O(CO3)2$H2O/silica/gold hybrid particles as a bifunctional agent for MR imaging and photothermal destruction of cancer cells", J. Mater. Chem., pp. 2147-2153 (Year: 2009).*

Yu-Dong Xiao, Ramachandra Paudel, Jun Liu, Cong Ma, Zi-Shu Zhang, and Shun-Ke Zhao. "MRI contrast agents: Classification and application (Review)." International Journal of Molecular Medicine, vol. 38, 2016, pp. 1319-1326. (Year: 2016).*

Gerion, D., et al., "Paramagnetic Silica-Coated Nanocrystals as an Advanced MRI Contrast Agent" J. Phys. Chem. C., pp. 12542-12551. (Year: 2007).*

* cited by examiner

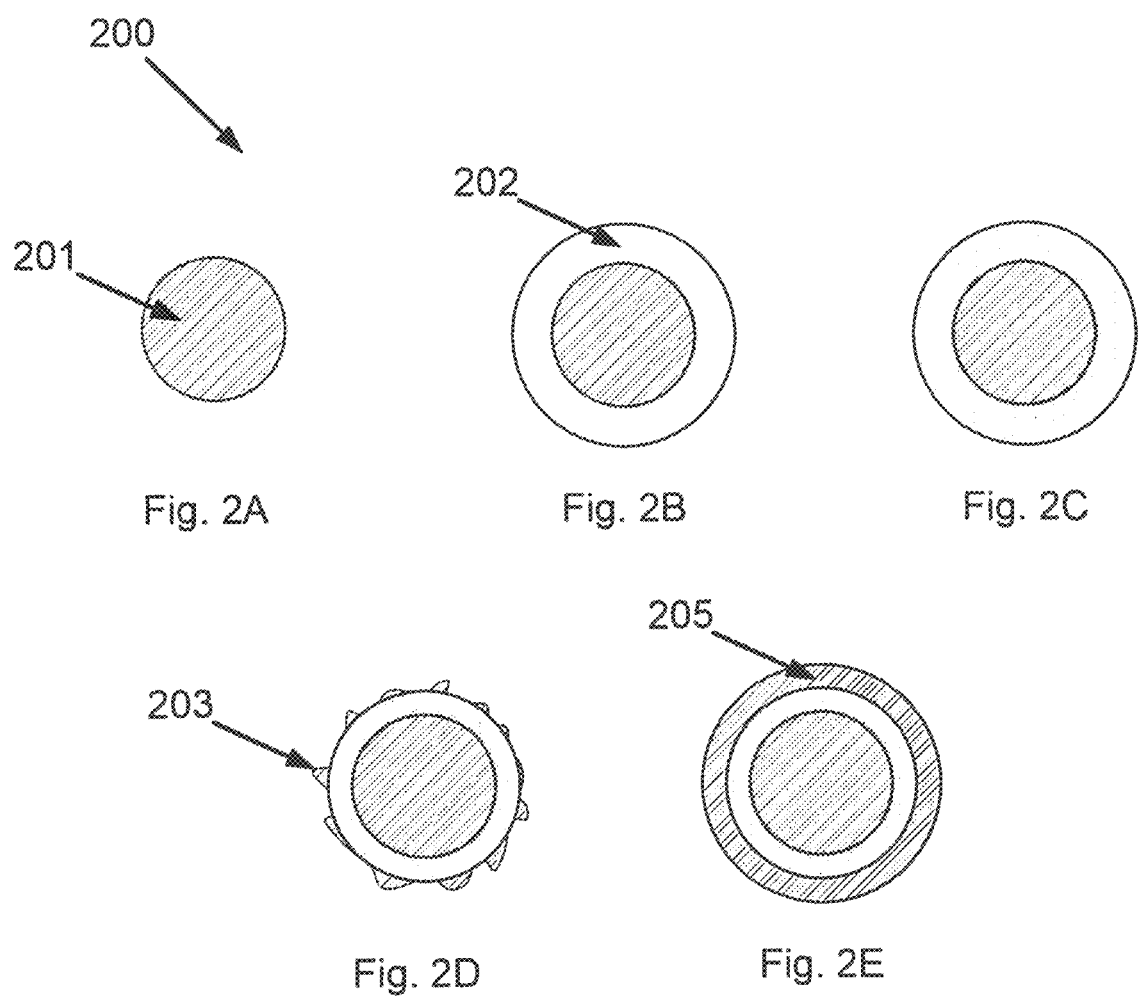

MULTIFUNCTIONAL FLUORESCENT AND MRI-ACTIVE NANOSTRUCTURE

CROSS-REFERENCE TO RELATED APPLICATIONS

This application is a continuation-in-part of application Ser. No. 14/823,891, which is a non-provisional patent application of U.S. Provisional Patent Application Ser. No. 62/035,716, filed on Aug. 11, 2014, and entitled: "Plasmonic sub-100 nm nanomatryoshkas that include contrast agents within layers of metal." The present application incorporates the subject matter of U.S. Provisional Patent Application Ser. No. 62/395,188, filed on Sep. 15, 2016, and entitled "Multifunctional MRI-Active and/or Fluorescent Nanostructure." Accordingly, this non-provisional patent application claims priority to U.S. Provisional Patent Application Ser. No. 62/035,716 and to U.S. Provisional Patent Application Ser. No. 62/395,188 under 35 U.S.C. § 119(e). U.S. Provisional Patent Application Ser. No. 62/035,716 and U.S. Provisional Patent Application Ser. No. 62/395,188 are hereby incorporated in their entirety.

STATEMENT REGARDING FEDERALLY SPONSORED RESEARCH OR DEVELOPMENT

The invention was made with government support under Grant Number CA 51886 awarded by the National institutes of Health. Additionally, the invention was made with support from the J. Evans Attwell-Welch Fellowship (L-C-0004). The government has certain rights in the invention.

BACKGROUND

In magnetic resonance imaging (MRI), there are two types of contrast agents: type 1 (T1) and type 2 (T2). T1 agents are positive contrast agents that make an image brighter on MRI phantoms. T2 agents are negative contrast agents that cause a darker image on MRI phantoms. Contrast agents for MRI lighten or darken MRI phantoms by modifying the relaxation time of the spins of protons in water. Commercial T1 contrast agents need to be in direct contact with water to produce its effect while T2 agents not need to be in direct contact with water.

SUMMARY

In one aspect, magnetic resonance imaging enhancement agent according to one or more embodiments may include a plurality of particles, each particle including a metal core; a dielectric shell disposed on the metal core including water and at least one MRI contrast agent; and a metal shell disposed on the exterior surface of the dielectric shell that encapsulates the dielectric shell.

In another aspect, a method of producing a magnetic resonance imaging enhancement particle may include coating a metal core with a dielectric to obtain a metal core with a dielectric coating; loading the dielectric coating with a MRI contrast agent to obtain a loaded dielectric coating; seeding the exterior of the dielectric coating with a metal to obtain a seeded dielectric coating; and coating the seeded dielectric coating with a metal plating solution to obtain the magnetic resonance imaging enhancement particle.

BRIEF DESCRIPTION OF DRAWINGS

FIG. 2A shows a step of a method of producing a magnetic resonance imaging enhancement agent in accordance with one or more embodiments.

FIG. 2B shows a step of a method of producing a magnetic resonance imaging enhancement agent in accordance with one or more embodiments.

FIG. 2C shows a step of a method of producing a magnetic resonance imaging enhancement agent in accordance with one or more embodiments.

FIG. 2D shows a step of a method of producing a magnetic resonance imaging enhancement agent in accordance with one or more embodiments.

FIG. 2E shows a step of a method of producing a magnetic resonance imaging enhancement agent in accordance with one or more embodiments.

DETAILED DESCRIPTION

Figure 1:
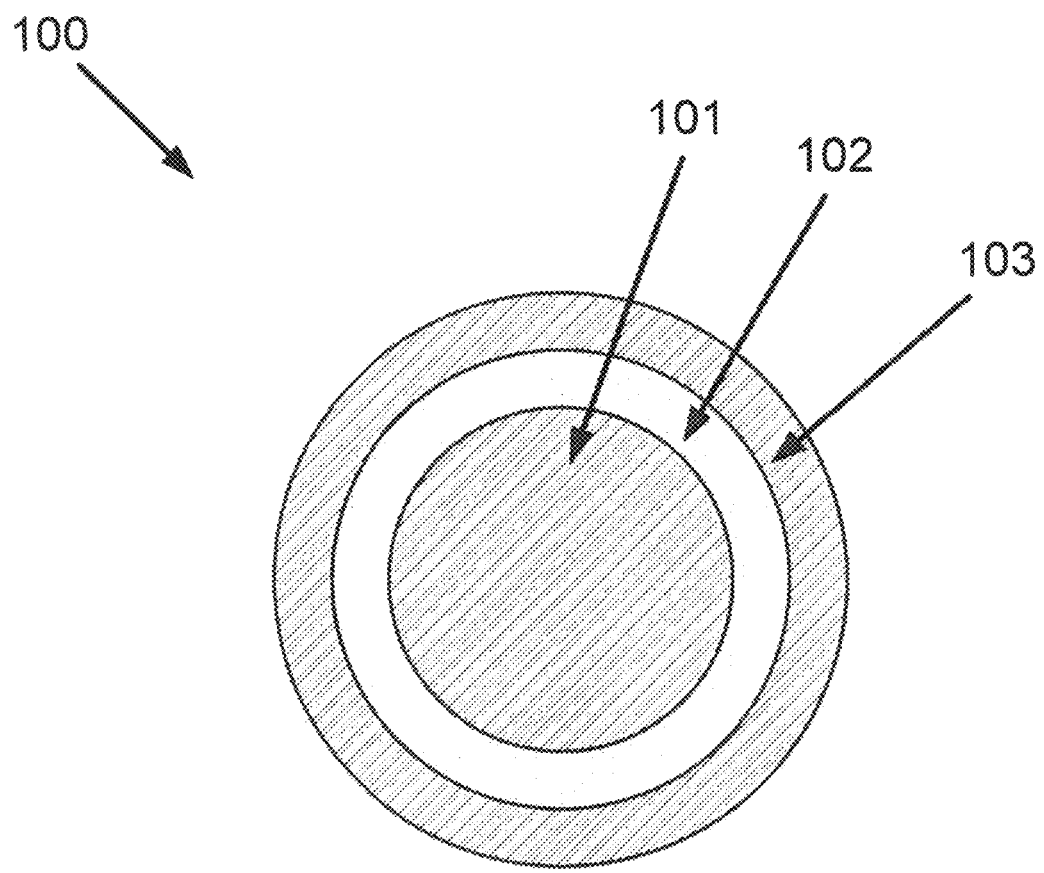
FIG. 1 shows a cross sectional view of a single particle of a magnetic resonance imaging contrast enhancement agent in accordance with one or more embodiments.

Specific embodiments will now be described in detail with reference to the accompanying figures. In the following description, numerous details are set forth to provide an understanding of the present disclosure. However, it will be understood by those skilled in the art that embodiments of the present disclosure may be practiced without these details and that numerous variations or modifications from the described embodiments may be possible.

In general, embodiments of the invention relate to a magnetic resonance imaging contrast enhancement agent comprising a plurality of particles with properties to enhance magnetic resonance imaging and/or photothermal ablation. Further, embodiments of the invention may combine the aforementioned magnetic resonance imaging enhancement agent with antibody and/or peptide targeting and/or photothermal therapeutic actuation.

In one or more embodiments of the invention, antibody targeting may be used such that the magnetic resonance imaging contrast enhancement agent may bind to the surface receptors of specific cell types. In the case of cancer therapy, the magnetic resonance imaging contrast enhancement agent may allow for the tracking the location of the particles in vivo. For example, magnetic resonance imaging may be used to follow the path of the particles or verify the quantity of particles at specific locations. Once verified, ablation of the targeted cells may be carried out by photothermal ablation. Further, in some embodiments the multifunctional particles described herein may be used for a variety of imaging applications, light induced drug release of therapeutic molecules, or hyperthermia treatment.

Additionally, one or more embodiments of the invention relate to methods, devices, materials, and/or systems including multifunctional fluorescent and MRI-active nanostructures. The multifunctional fluorescent and MRI-active nanostructures may enable imaging, targeted drug delivery, and photothermal therapy to be conducted. Further, the multifunctional fluorescent and MRI-active nanostructures may be used to perform other processes without departing from the invention.

In one or more embodiments of the invention, the multifunctional fluorescent and/or MRI-active nanostructures may be nanoparticles. That is, all dimensions of the multifunctional fluorescent and/or MRI-active nanostructures may be less than 100 nm. Each or a portion of the nanoparticles may be both fluorescent-active and MRI-active, e.g., generate fluorescence and/or MRI contrast when imaged using an appropriate technique.

In one or more embodiments of the invention, the magnetic resonance contrast enhancement agent may be used in other medical imaging techniques including Positron Emission Tomography-Computed Tomography (PET-CT), Positron Emission Tomography-Magnetic Resonance Imaging (PET-MRI), or Fluorescence Optical Imaging (FOI).

In another embodiment, an image enhancement agent may be substituted for the magnetic resonance image contrast enhancement agent or another image enhancement agent may be added to the magnetic resonance imaging contrast enhancement agent. The substituted or added image enhancement agent may be used with other medical imaging techniques. For example, a radionuclide may be substituted for or added to the magnetic resonance imaging contrast enhancement agent for use with Positron Emission Tomography. In another example, a fluorophore such as indocyanine green (ICG), Cy7, or IR800 may be substituted for or added to the magnetic resonance imaging contrast enhancement agent for use with FOI.

In one or more embodiments of the invention, the particles discussed herein may include a core, an encapsulating layer (which may also be referred to herein as a shell), and an interstitial layer. The interstitial layer may be disposed between the core and the encapsulating layer.

In one or more embodiments, the core may be a metal. In one or more embodiments the metal may be gold, silver, platinum, palladium, or copper. However, the core may be a different metal than those listed above without departing from the invention. In one or more embodiments of the invention, the encapsulating layer may encapsulate the core and the interstitial layer. The encapsulating layer may be a metal. The metal may be, for example, gold, silver, platinum, palladium, or copper. However, the encapsulating layer may be a different metal than those listed above without departing from the invention. In one or more embodiments, the encapsulating layer may have other materials disposed on an exterior side of the encapsulating layer. For example, polymeric, ceramic, targeting molecules, fluorescing material, MRI-contrast agents or other materials may be disposed on an exterior surface of the encapsulating layer. In one or more embodiments of the invention, the encapsulating layer may include a fluorescing material. For example, the fluorescing material may be attached or chemically linked to the encapsulating layer. The fluorescing material may be, for example, a fluorescing dye. However, other fluorescing materials may be used without departing from the invention. In one or more embodiments of the invention, the exterior of the encapsulating layer may be functionalized with molecules including polyethyleneglycol (PEG), DNA/aptamers, proteins, polypeptides, antibodies, or other polymeric molecules.

In one or more embodiments of the invention, the interstitial layer may be disposed between the core and the encapsulating layer. In some embodiments of the invention, the interstitial layer may encapsulate the core. In other embodiments of the invention, the interstitial layer may be disposed on only a portion of the core, e.g., only cover a portion of the core. For example, in one or more embodiments, the interstitial layer may only be disposed on a portion of the total surface area of the core.

In one or more embodiments of the invention, the interstitial layer may be a dielectric material. The dielectric material may be, for example, silica. The dielectric material may be other dielectric materials without departing from the invention. In one or more embodiments, the interstitial layer may be made of polydopamine (PDA).

In one or more embodiments of the invention, the interstitial layer may include at least one magnetic resonance imaging (MRI) active material. In one or more embodiments of the invention, the MRI active material is a T1 contrast material. In one or more embodiments of the invention, the MRI active material is a transition metal and/or a lanthanide. In one or more embodiments of the invention, the transition metal and/or a lanthanide are selected from gadolinium (III), iron (II), iron (III) and/or manganese (II). The interstitial layer may include any number, type, and/or combination of metal ions without departing from the invention.

Fe(III) based contrast agent may be able to overcome some limitations for Gd(III). Specifically, higher magnetic field strength is preferred in clinical use due to greater signal to noise, higher spatial resolution, and reduced acquisition times. However, the $T_1$ relaxivity of molecular Gd(III) compounds typically decreases as magnetic field strength increases. Conversely, the $T_1$ relaxivity of molecular Fe(III) compounds generally increases with increasing field strength. Thus, multifunctional particles using Fe(III) may be better suited for clinical applications. In addition, Gd(III)

contrast agents have known toxicity concerns associated with nephrogenic systemic fibrosis (NSF), while Fe(III) has lower toxicity concerns.

Mn(II) based contrast agent may be able to overcome some limitations for Gd(III). As mentioned above, there are toxicity concerns with gadolinium based contrast agents. Manganese(II) is an alternative paramagnetic metal ion used in contrast agents and is biogenic. Although Mn(II) is less paramagnetic than Gd(III), Mn(II) is more labile and has a shorter water-metal ion distance. This may result in increased interaction with neighboring water molecules which can partially compensate for the lower paramagnetism. Paramagnetic metal ions such as Gd(III), Mn(II), and Fe(III) are T1 contrast agents and produce a brighter image when operated under T1-weighted MRI.

In one or more embodiments of the invention, the interstitial layer may include S-2-(4-Isothiocyanatobenzyl)-1,4, 7,10-tetraazacyclododecane-1,4,7,10 tetra acetic acid (DOTA-SCN) chelate and/or any other chelates. In particular, the chelates may include —SCN, NCN, or OCN groups. These particular groups may allow for the material to be chemically bonded to the dielectric layer, particularly if the dielectric layer is silica that has been doped with 3-aminopropyl-triethoxysilane (APTES), as will be discussed below. When included, a chelant can chelate the transition metal and/or lanthanide MRI active material. Chelating the transition metal and/or lanthanide MRI active material within the interstitial layer of the multifunctional particles may solve issues commonly observed for non-chelated transition metal and/or lanthanide MRI active materials, including high toxicity, poor sensitivity, low stability, and their rapid clearance from the body. Without being bound by theory, it is believed that incorporating the chelants may help to accomplish the above by effectively concentrating and stabilizing the transition metal and/or lanthanide MRI active material within the interstitial layer which prolongs valuable imaging time and the time available for other uses of the multifunctional particles. Further, when the chelates include an SCN, NCN, or OCN group the chelate may be chemically bonded and thereby secured to the silica of the dielectric layer. In embodiments where PDA is used as the dielectric layer, the chelates (also the fluorescing material, phosphorescent material, or luminescent material described below) may be chemically attached to the PDA prior to coating the core with the PDA.

In one or more embodiments of the invention, the interstitial layer may include fluorine containing molecules. In one or more embodiments of the invention, the interstitial layer includes fluorine doped silica. In one or more embodiments, the interstitial layer includes fluorosilane or perflubron (perfluorooctyl bromide) molecules. The inclusion of fluorine containing molecules in the interstitial layer may allow for $^{19}$F-MRI tracking, which is a promising tracking technique due to the lack of fluorine naturally in the body.

In one or more embodiments of the invention, the interstitial layer may include a fluorescing, phosphorescent, or luminescent material. The fluorescing material may be, for example, quantum dots, a fluorescing dye, or isothiocyanate (SCAN)-functionalized near IR dye. The inclusion of a dye in the interstitial layer may reduce the photobleaching of the dye and thus extend the usefulness of the dye. Other fluorescing materials may be used without departing from the invention. Any known phosphorescent or luminescent material may be included in the interstitial layer. In one or more embodiments, the fluorescing, phosphorescent, or luminescent material may include a terminal thiocyanate group, which allows for the material to be chemically bonded to the dielectric layer, particularly if the interstitial layer is silica doped with APTES. However, in one or more embodiments, the dye is not chemically bonded to the interstitial layer so as to reduce chemical bonding competition with a metal chelate that is functionalized to allow for bonding with the interstitial layer.

The interstitial layer may include other metals, materials, dyes, and/or chemicals without departing from the invention.

In one or more embodiments of the invention, the magnetic resonance imaging contrast enhancement agent comprises particles including metal shells that are used to encapsulate imaging agents within an interstitial layer of dielectric to form a magnetic resonance imaging contrast enhancement agent. In one or more embodiments of the invention, the dielectric may be silica. In one or more embodiments of the invention, the overall dimension of the individual particles is less than 100 nm in diameter. In one or more embodiment, the metal shell is gold or silver.

In one or more embodiments, the particles comprising the magnetic resonance imaging contrast enhancement agent include a metal core within the interstitial layer of dielectric. When a metal core is present in the interstitial layer of dielectric, the particles include a metal core, an interstitial layer of dielectric, and a metal shell. The dielectric may be silica ($SiO_2$) or other dielectric material. The particle-in-shells design may be referred to as a nanomatryoshka and abbreviated as "NM" in some instances. In one or more embodiments of the invention, the metal core is gold or silver. In one or more embodiments, the metal core may be rod shaped, star shaped, or a cube. In one embodiment of the invention, nanomatryoshkas may support plasmon resonances. A plasmon resonance is the collective oscillation of conduction band of electrons within a metal surface upon excitation with an external electromagnetic field. The plasmon resonance concentrates the external electromagnetic field to enhance the properties of contrast agents attached nearby the metal surfaces. The plasmon resonance of the metal core and the metal shell of nanomatryoshka particles may hybridize to give rise to a new hybrid mode, not present in particles that only include a metal shell. The new hybrid mode has a lower plasmon energy which causes a plasmon resonance between. 200 nm and 1200 nm for nanomatryoshkas having a diameter of less than 100 nm. The nanomatryoshkas may have a large absorption cross-section that is tunable to a near-infrared laser (~800 nm). Light absorbed near 800 nm may be transduced to heat that can be efficiently used, for example, to destroy cancer cells in photothermal ablation therapy.

In one or more embodiments, the core of the particles described herein may be made of gold and may have a spherical or rod shape. The composition and specific shape of the gold core may allow for tailoring the multifunctional fluorescent and MRI-active nanostructure to have a plasmon resonance that is tuned to the near-IR window of the electromagnetic spectrum (i.e., from about 700 nm to 2500 nm). Near-infrared light can penetrate biological tissues more efficiently than visible light because tissue scatters and absorbs less light at the longer NIR wavelengths. In one or more embodiments, the particles according to the present disclosure may have a plasmon resonance that peaks in a region between about 1000 nm and 1350 nm. These particular wavelengths may be particularly preferred for in vivo imaging because they can improve signal-to-noise ratios by reducing background noise caused by tissue. In one or more embodiments, the particles according to the present disclosure that have a plasmon resonance that peaks in a region between about 1000 nm and 1350 nm may include a gold nanorod core.

In accordance with one or more embodiments of the invention, FIG. 1 illustrates a cross sectional view of a single particle of a magnetic resonance imaging contrast enhancement agent (100), or other particle according to the present invention. The particle includes a metal core (101), dielectric shell (102), and a metal shell (103). The dielectric shell (102) may be silica. The dielectric shell (102) may be other dielectric materials without departing from the invention.

In one or more embodiments, the dielectric shell is doped with 3-aminopropyl-triethoxysilane. The metal core (101) is approximately spherical in one or more embodiments. In further embodiments, the metal core (101) is rod shaped, star shaped, or a cube. The outer dimension of the metal core (101) is less than 40 nanometers. In one or more embodiments the metal core (101) is gold or silver.

The dielectric shell (102) may be less than 20 nm thick and disposed on the metal particle (101). The dielectric shell (102) may have a rough outer surface. In one or more embodiments, the dielectric shell (102) is loaded with a solution of water and a type 1 contrast agent. A type 1 contrast agent appears brighter in a magnetic resonance imaging phantoms. In one or more embodiments, the dielectric shell (102) is loaded with a solution of water and a type 2 contrast agent. In one or more embodiments, the dielectric shell (102) is loaded with a solution of water, a type 1 contrast agent and a type 2 contrast agent. In one or more embodiments, the type 1 contrast agent is a lanthanide ion. In one or more embodiments, the lanthanide ion is gadolinium (III). In one or more embodiments, the type 1 contrast agent is manganese oxide or ultra-small iron oxide (USIO, diameter <5 nm) and the type 2 contrast agent is iron oxide. In one or more embodiments, the type 1 contrast agent may be transition metal ions selected from Mn(II), Fe(II), and Fe(III). In one or more embodiments of the invention, the type 1 contrast agent is chelated with diethylene triamine pentaacetic acid (DTPA).

The metal shell (103) may be disposed on the dielectric shell (102). The metal shell may be between 1 and 20 nm thick and encapsulates the dielectric shell (102) and metal particle (101).

The radius of the metal particle (101), thickness of the dielectric shell (102), and thickness of the metal shell (103) are selected to support a plasmon resonance centered at greater than 400 nm and less than 1200 nm while keeping the total outer dimension of the particle below 100 nm. In one or more embodiments of the invention, the radius of the metal particle (101), thickness of the dielectric shell (102), and thickness of the metal shell (103) are selected to support a plasmon resonance centered at about 810 nm while keeping the total outer dimension of the particle below 100 nm.

In accordance with one or more embodiments of the invention, FIGS. 2A-2E show a series of panels illustrating a method of producing a magnetic resonance imaging enhancement agent, or other particle according to the present invention. Each panel illustrates a cross sectional view of a part of the production method (200). One or more parts shown in FIG. 2 may be omitted, repeated, and/or performed in a different order among different embodiments of the invention. Accordingly, embodiments of the invention should not be considered limited to the specific number and arrangement shown in FIG. 2.

The method (200) starts with a metal core (201) as shown in panel (A). In FIG. 2A, the metal core is drawn as a circle but could be a cube, rod, or star shaped. A dielectric shell (202), shown in FIG. 2B, is deposited onto the metal core (201) by a wet chemical process which is described below. In one or more embodiments, the dielectric shell may be doped/functionalized with chelate molecules which can enable metal ion chelation. Following the deposition of the dielectric shell (202), the dielectric shell (202) may be submerged in a first solution that includes water and a type 1 contrast agent for a predetermined time. In one or more embodiments, the predetermined time may be about 14 hours. Other predetermined times may be used without departing from the invention. In one or more embodiments, the type 1 contrast agent is a lanthanide. In one or more embodiments, the lanthanide is gadolinium. In one or more embodiments, the type 1 contrast agent is manganese oxide or iron oxide. When the dielectric shell is doped/functionalized with chelate molecules the type 1 contrast agent may be chelated by the chelate molecules, thereby increasing the efficiency of the uptake of the type 1 contrast agent from solution.

Submerging the dielectric shell (202) results in water and a lanthanide being loaded into the dielectric shell (202) as illustrated in FIG. 2C. The lanthanide may be chelated by diethylene triamine pentaacetic acid or other chelates indicated above. Following submersion in the first solution, the dielectric shell (202) may be submerged in a second solution including gold colloid produced through the reaction of sodium hydroxide, aqueous tetrakis(hydroxymethyl) phosphonium chloride, and aqueous chloroauric acid. The second solution both etches the dielectric shell (202) to reduce the thickness to a desired thickness and seeds the dielectric shell (202) with metal (203) as shown in FIG. 2D. In one or more embodiments, the seeded metal (203) is silver or gold. Seeding the dielectric shell (202) results in small patches of metal (203) that are distributed over the dielectric shell (202) and adhered to the dielectric shell (202). Lastly, after etching and seeding the dielectric shell (202), a metal shell (205) is plated on the exterior surface of the dielectric shell (202) as shown in FIG. 2E. In one or more embodiments, the metal shell is silver or gold.

In one or more embodiments, a fluorescing, phosphorescent, or luminescent material may also be added to the interstitial/dielectric layer by incubating the particles shown in either of FIG. 2B-2D with a solution containing a fluorescing, phosphorescent, or luminescent material. That is, the fluorescing, phosphorescent, or luminescent material may be loaded before loading any other material into the interstitial/dielectric layer, simultaneously loaded with the metal ion contrast agent, after loading the interstitial/dielectric layer with metal ion contrast agent, or after seeding gold colloid to the surface of the interstitial/dielectric layer but prior to plating the metal shell onto the interstitial/dielectric layer using a plating solution.

In one embodiment of the invention, magnetic resonance imaging contrast enhancement agent is produced using a four step process including coating gold or other core material particles with APTES-doped dielectric, loading water and Gadolinium or other contrast material into the APTES-doped dielectric coating, etching the dielectric coating and seeding the dielectric coating with gold, and coating the dielectric coating with gold. Additional detail about a particular embodiment of the four step process is included below.

Step 1: Coating gold particles with APTES-doped silica. Gold colloid (50 nm citrate NanoXact Gold, nanoComposix) is coated with silica doped with 3-aminopropyl-triethoxysilane (APTES) by a modified Stöber process. (APTES is used as a binding site for gold colloid.) 21 mL of gold colloid ($7.0\times10^{10}$ particles/mL, citrate capped 50 nm Au sphere, NanoComposix) is added under stirring to an Erlenmeyer flask with a ground glass joint. Next, 180 mL of 200 proof ethanol (Decon Labs) and, 1.8 mL of ammonium hydroxide (28-30%, EMD Chemicals) are added to the gold colloid. Then, 36 µL of a solution of 10% tetraethoxysilane (TEOS, SIT7110.2, Gelest) in ethanol and 36 µL of 10% APTES (SIA0610.1, Gelest) in ethanol is added to the gold colloid. The gold colloid is sealed and stirred for 50 min at room temperature and then the gold colloid is cooled to 4° C. and stirred for 19 h. The gold colloid is transferred to a dialysis membrane (Spectra/Por 6, MWCO=10000, Spectrum Labs), previously washed with Milli-Q grade water to remove residual chemicals and then with ethanol to remove excess water. The gold colloid is then dialyzed in 1 gallon of 200 proof ethanol for at least 12 h at room temperature to remove ammonium hydroxide and the remaining free silanes (TEOS and APTES) from the gold colloid. The gold colloid is then cooled to 4° C. and centrifuged for 30 min at 2500 ref to form a number of first pellets (the solution was centrifuged in aliquots of ~15 mL using 50 mL plastic tubes). If the supernatant is still red, the centrifugation is repeated to recoup more particles in the form of additional first pellets.

Step 2: Loading water and Gadolinium into the APTES-doped silica coating. Disperse the first pellets by sonication in solution including a total volume of 7.5 mL of water solution, 10 mg/mL $GdCl_3$, and 15 mg/mL Gd-DTPA. Stir the solution of nanoparticles with gadolinium compounds for 14 h at room temperature. After stirring, the centrifuge the solution at 2000 ref for 30 mins to form a second pellet. Then centrifuge the supernatant at 2500 ref for 30 mins to form a third pellet. Disperse the second and third pellets in 700 µL of water, by sonicating for 30 seconds. Centrifuge the 700 µL of solution at 2000 ref for 20 mins to form a fourth pellet. Disperse the fourth pellet in 1 mL, of water by sonicating for 30 seconds to form an APTES-doped silica coated gold colloid.

Step 3: Etching the silica coating and seeding the silica coating with gold. First, synthesize a Duff colloid by quickly, under rapid stirring, adding 1.2 mL of 1 M NaOH to 180 mL of $H_2O$, followed by adding 4 mL of a 1.2 mM aqueous tetrakis(hydroxymethyl) phosphonium chloride (THPC, 80% solution in $H_2O$, Sigma). Stir for 5 min and then add 6.75 mL of 1% (w/v) aqueous chloroauric acid ($HAuCl_4.3H_2O$, Sigma-Aldrich). Refrigerate the solution for at least 2 weeks to form a Duff colloid.

Second, add 20 mL of Duff colloid to 50 mL plastic centrifuge tubes, followed by 300 µL of 1 M NaCl and 1 mL of APTES-doped silica coated gold colloid. Vortex and sonicate the solution for 10 min. After vortexing and sonicating, incubate the solution for 12 h at room temperature. Incubation in the solution etches and seeds with metal the APTES-doped silica coated colloid particles. After the incubation, sonicate the solution for 30 seconds and then centrifuged for 25 min at 900 ref (10 mL in each tube) to form a number of fifth pellets. Disperse the fifth pellets in 800 µL of water by sonication for 1 min and transfer to several 2 mL centrifuge tubes. Centrifuge the solution for 2.0 min at 1100 ref to form a series of sixth pellets. Disperse the sixth pellets in 1 mL of water by sonicating for 1 min to form an etched and seeded particle solution.

Step 4: Coating the etched and seeded particles with gold. A metal shell of gold around the etched and seeded particles was performed using a plating solution as a source of $Au^{3+}$. A plating solution is prepared by mixing 200 mL of water, 50 mg of anhydrous potassium carbonate ($K_2CO_3$), and 3 mL of 1 wt % aqueous chloroauric gold solution followed by aging for 12-19 h. The reduction of $Au^{3+}$ into a metal shell of Au around the silica coating is performed in a 4.5 mL methacrylate cuvette with a plastic cap. Add a volume of 1.5 mL of plating solution to the cuvette followed by 20-60 µL of the etched and seeded particle solution. Next, add 7.5 µL of formaldehyde dropwise inside the cap, and close the cuvette. Shake the corvette containing the solution for about 1 min to complete the plating process. The formaldehyde initiated the plating process by reduced the gold ions included in the plating solution.

Examples of magnetic resonance imagining contrast enhancement agents in accordance with one or more embodiments were characterized using a transmission electron microscope.

Figure 3A:
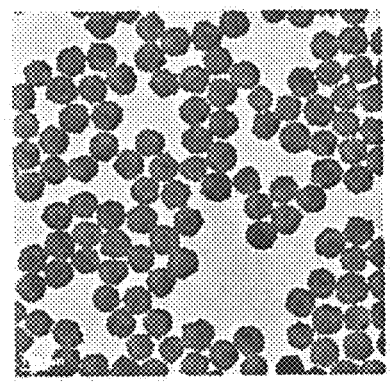
FIG. 3A shows a transmission electron microscope (TEM) image of a plurality of particles of a magnetic resonance imaging contrast enhancement agent in accordance with one or more embodiments.

FIG. 3(A) shows a transmission electron microscope image of the magnetic resonance imaging contrast enhancement agent in accordance with one or more embodiments of the invention. The magnetic resonance imaging contrast enhancement agent is mono-dispersed in size and the outer dimension of each particle is less than 100 nm.

Figure 3B:
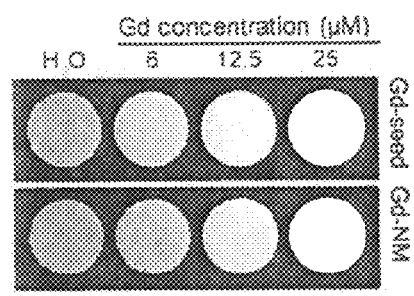
FIG. 3B shows an extinction spectrum of a plurality of particles of a magnetic resonance imaging contrast enhancement agent in accordance with one or more embodiments.
Figure 3C:
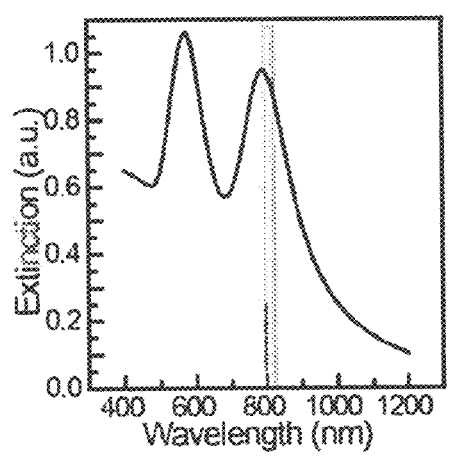
FIG. 3C shows the T1 enhancement of a plurality of particles of a magnetic resonance imaging contrast enhancement agent in accordance with one or more embodiments.

The plasmon resonance of the magnetic resonance imaging contrast enhancement agent has been tuned to 810 nm as indicated in FIG. 3(C).

FIG. 3(B) shows the T1 enhancement of a magnetic resonance imaging contrast enhancement agent in accordance with one or more embodiments of the invention (labeled as Gd-seed) and Gadolinium-DTPA (labeled as Gd-NM). The magnetic resonance imaging contrast enhancement agent provides superior T1 enhancement to Gadolinium-DTPA for all levels of gadolinium concentration as indicated by the color of each circle in the plot.

Figure 3D:
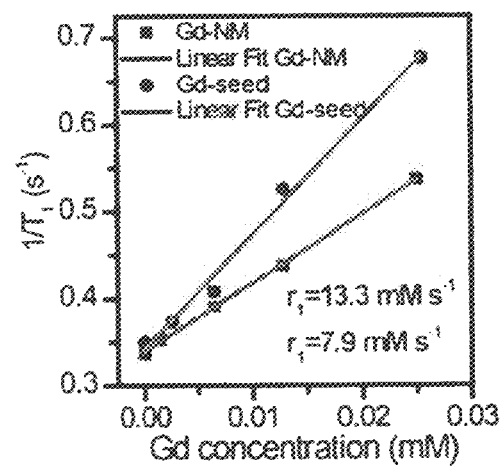
FIG. 3D shows the relaxivity of a plurality of particles of a magnetic resonance imaging contrast enhancement agent in accordance with one or more embodiments.

FIG. 3(D) shows the relaxivity of a magnetic resonance imaging contrast enhancement agent in accordance with one or more embodiments of the invention and Gadolinium-DTPA. As seen, the magnetic resonance imaging contrast enhancement agent provide superior relaxivity over Gadolinium-DTPA for all levels of concentration as indicated by the greater slope of the magnetic resonance imaging contrast enhancement agent.

In one or more embodiments of the invention, a particle according to the present invention may be formed by growing an interstitial layer around a metal core. The metal core may be a sphere that has a radius between about 5 and 60 nm, or between about 10 and 50 nm. In one or more embodiments, the metal core is rod-shaped or cuboidal.

The interstitial layer may be silica or fluorine doped silica. In one or more embodiments, the interstitial/dielectric layer may be from about 5-40 nm thick, or more particularly less than 20 nm thick. In one or more embodiments, the core may be coated with a silica interstitial layer that is doped with 3-aminopropyl-triethoxysilane (APTES), as discussed above. The use of APTES in the silica layer adds amino groups to the silica that can later act as binding sites for molecules that have a functionality capable of reacting with the amino groups. For example, molecules that include SCN, NCN, or OCN groups may be capable of reacting with the amino group to form a covalent bond that strongly attaches the molecule to the interstitial layer. In one or more embodiments, chelant molecules that include SCN, NCN, or OCN may be doped directly into the APTES containing silica layer during the formation of the silica layer by including the molecules during the process/reaction to create the silica layer. In one or more embodiments, chelant molecules that include SCN, NCN, or OCN may be doped into the APTES containing silica layer after the formation of the silica layer by contacting the core particles having a silica interstitial layer thereon with a solution including chelant molecules that include SCN, NCN, or OCN groups.

Figure 4A:
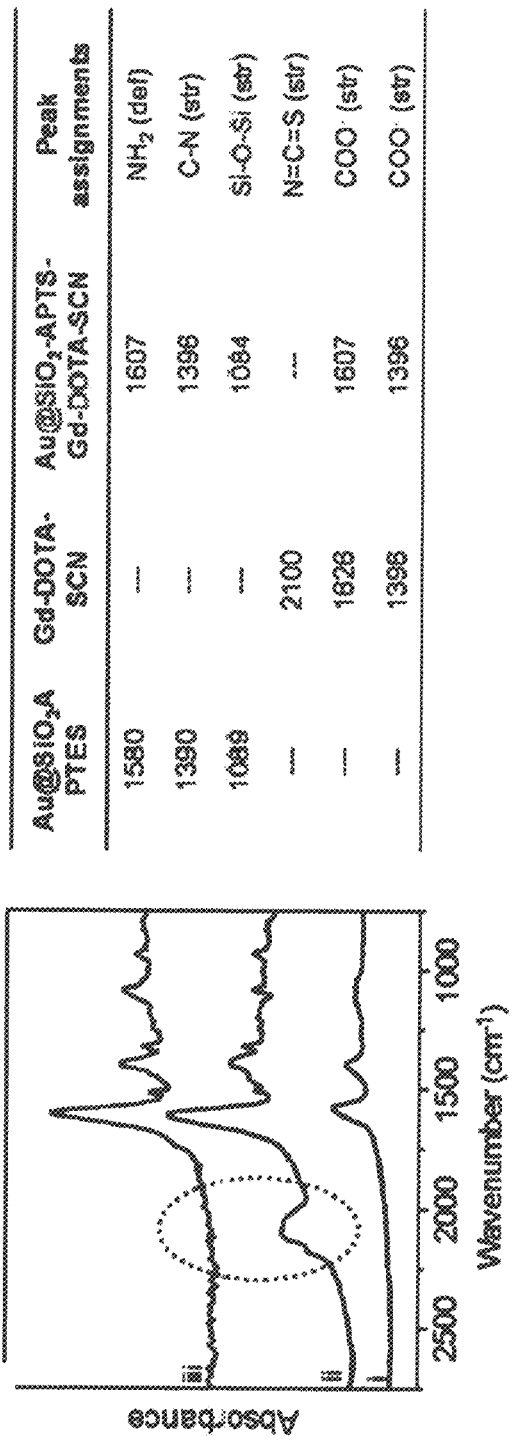
FIG. 4A shows experimentally obtained FTIR spectra for (top) Au@$SiO_2$-APTES, (middle) Gd-DOTA-SCN, and (bottom) Gd-DOTS-SCN doped $SiO_2$-coated gold particles.
Figure 4B:
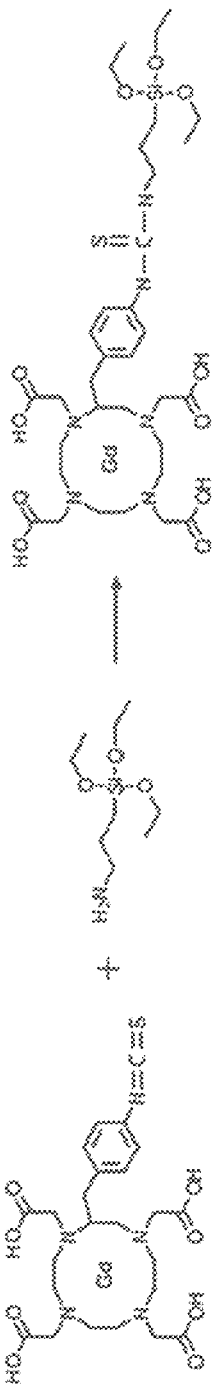
FIG. 4B shows a reaction scheme where a chelant containing a SCN group and a chelated gadolinium ion (Gd-DOTA-SCN) chemically reacts with an amino group available from APTES

FIG. 4B shows a reaction scheme where a chelant containing a SCN group and a chelated gadolinium ion (Gd-DOTA-SCN) chemically reacts with the amino group available from APTES, thereby forming a covalent bond between the chelant and the amino group from APTES. FIG. 4A shows experimentally obtained FTIR spectra for (top) Au@SiO$_2$-APTES, (middle) Gd-DOTA-SCN, and (bottom) Gd-DOTA-SCN doped SiO$_2$-coated gold particles. The clear disappearance of the ~2100 cm$^{-1}$ peak in the bottom spectrum indicates that a chemical bond has been formed between the amino group of the APTES and the SCN group of the Gd-DOTA-SCN. Any of the MRI contrast agents discussed herein may be chelated and then chemically bound to an APTES doped silica interstitial layer in a similar manner.

Figure 5:
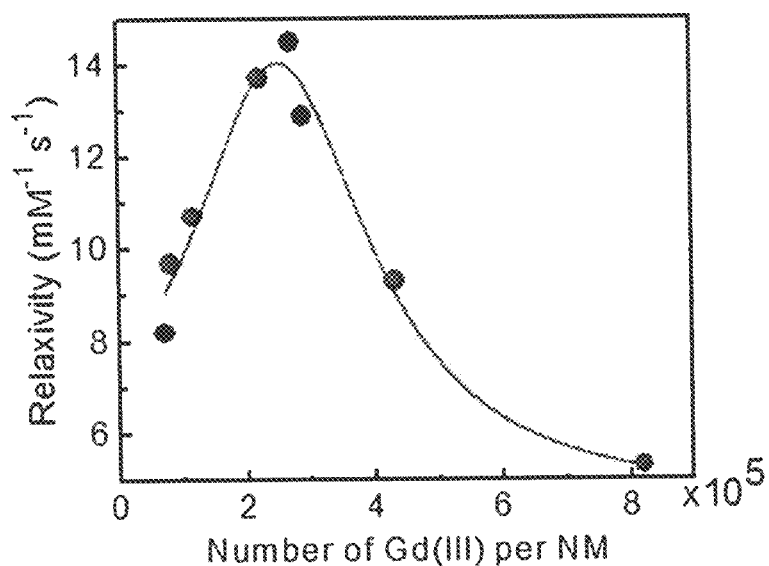
FIG. 5 shows a plot of the $r_1$ relaxivity of Gd(III) containing particles as a function of ion concentration per particle.
Figure 6:
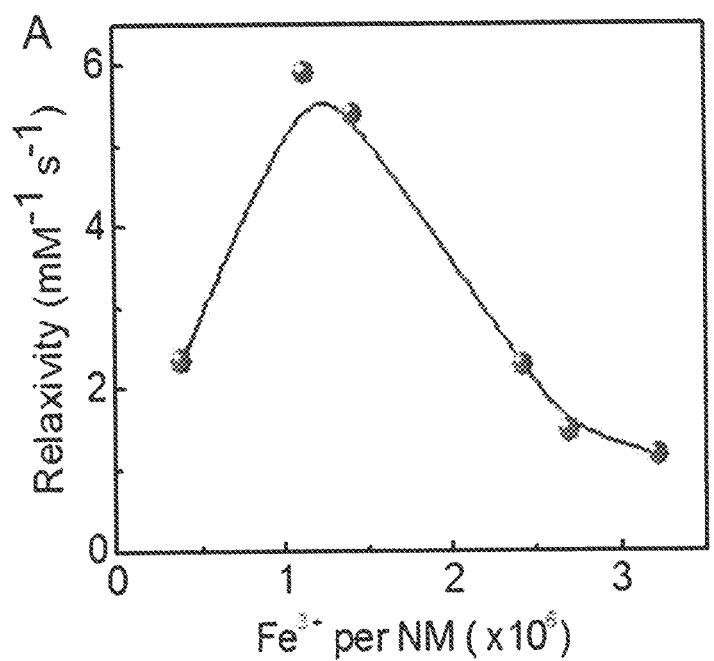
FIG. 6 shows a plot of the $r_1$ relaxivity of Fe(III) containing particles as a function of ion concentration per particle.

A MRI active material may be loaded into the interstitial layer. The MRI active material may be loaded into the interstitial layer by incubating the particles containing an interstitial layer with a metal salt. The metal salt may include a metal ion selected from gadolinium, iron, and/or manganese. In one or more embodiments, the duration of the incubation may be from about 1 to 20 hours, or from about 2 to 15 hours. In one or more embodiments, the duration of incubation may be less than about 5 hours. One will appreciate that the inclusion of a chelant molecule in the interstitial layer, as described above, may reduce the time period for incubation as the chelant may increase the uptake of the MRI active metal. Further, the incubation period may vary depending on the MRI active metal used, as different loading levels may be more appropriate for certain metals in order to achieve optimal MRI contrast levels. For example, FIGS. 5 and 6 show the r$_1$ relaxivity of Gd(III) and Fe(III) containing particles (i.e., particles containing the ions loaded into an interstitial layer between a gold core and a gold shell) as a function of ion concentration per particle, respectively. Typically, a higher relaxivity value is desired in order to increase MRI contrast levels. Thus, one can see from FIGS. 5 and 6 that for each MRI contrast agent containing system the relaxivity is increased as the loading increases before decreasing at higher loadings. The decrease at higher loadings is presumably due to increased interaction between metal ions as their concentration increases.

Figure 7A:
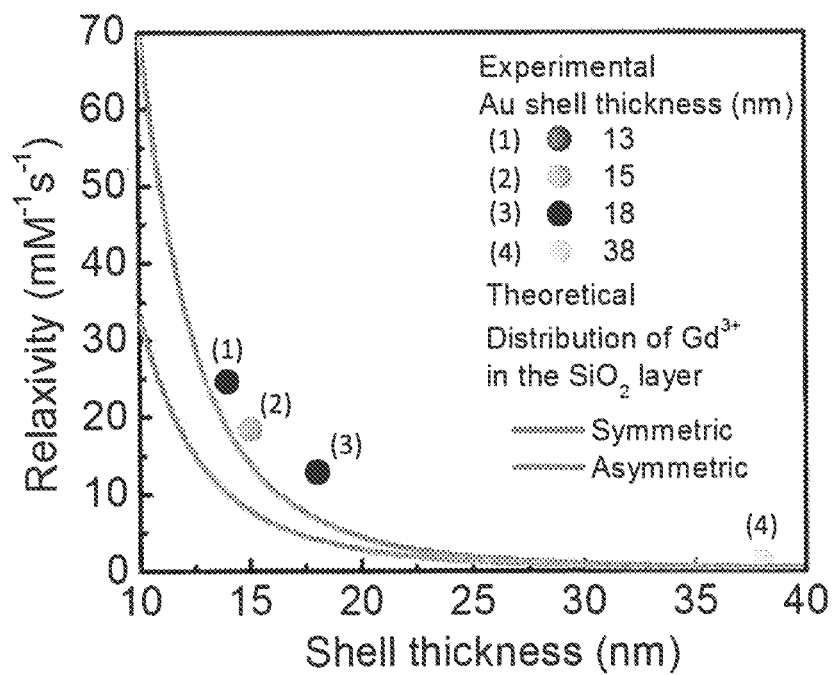
FIG. 7A shows a plot of the relaxivity change of samples including Gd(III) containing particles as a function of gold shell thickness.
Figure 7B:
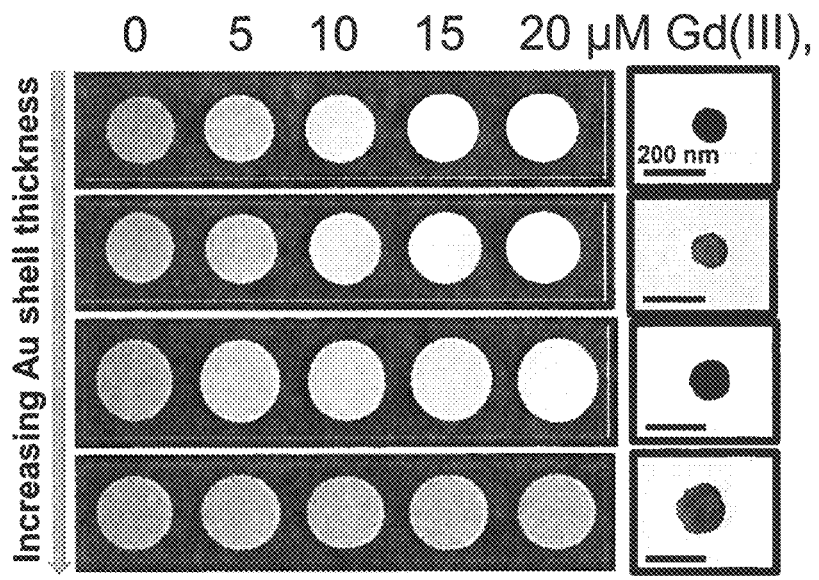
FIG. 7B shows the MRI contrast change of samples including Gd(III) containing particles as a function of gold shell thickness.
Figure 8A:
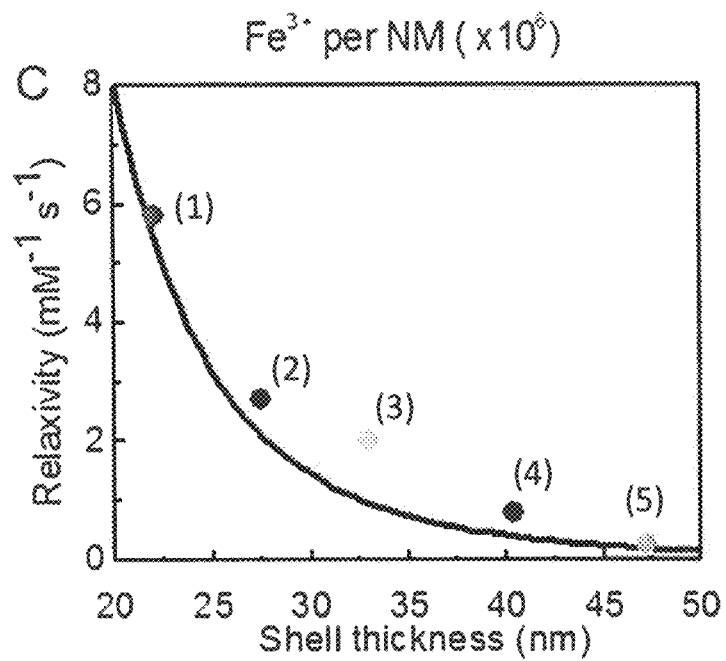
FIG. 8A shows a plot of the relaxivity change of samples including Fe(III) containing particles as a function of gold shell thickness.
Figure 8B:
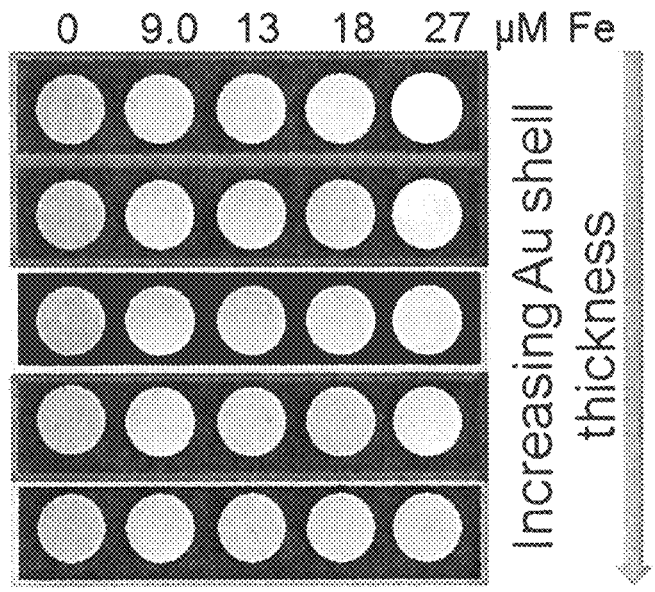
FIG. 8B shows the MRI contrast change of samples including Fe(III) containing particles as a function of gold shell thickness.

An encapsulating layer may be formed that encapsulates the interstitial layer and core. The encapsulating layer may be formed by seeding the surface of the interstitial layer with particles followed by contacting the seeded surface with a plating solution containing metal ions to be plated. The thickness of the encapsulating layer may be controlled by controlling at least one of the incubation time in the plating solution and the concentration of metal ions to be plated in the plating solution. Too thick of an encapsulating layer may impair the ability of the MRI contrast agents to impart MRI contrast as a thick shell will increase the separation distance between the MRI contrast agents and the water protons in the system to be examined. For example, FIGS. 7A-7B show the relaxivity and MRI contrast change, respectively, of Gd(III) containing particles as a function of gold shell thickness. The results demonstrate that the relaxivity and contrast decreases as shell thickness is increased. FIGS. 8A-8B show the relaxivity and MRI contrast change, respectively, of samples of Fe(III) containing particles as a function of gold shell thickness. In FIG. 8A the particles have a gold shell thickness as follows (1) 22 nm, (2) 27 nm, (3) 33 nm, (4) 40 nm, (5) 47 nm.

In one or more embodiments of the invention, the thickness of the encapsulating layer is configured to enable protons from water or other materials that may be disposed near the particle/nanostructure to interact with the MRI active material in the particle/nanostructure. In one or more embodiments, the thickness of the encapsulating layer may be from about 1 nm to about 100 nm, or from about 5 nm to about 50 nm, or from about 10 nm to about 35 nm.

Prior to completely encapsulating the interstitial layer. The particles may be incubated with a fluorescing material. The fluorescing material may be a fluorescing dye. In one or more embodiments, a fluorescent dye may be chosen so that its maximum emission value overlaps or otherwise corresponds to the plasmon resonance of the particle, which may result in maximum enhancement of the fluorescent signal. In one or more embodiments, the fluorescent dye may be added to the middle of the interstitial layer as inclusion of the dye in the innermost and outermost portion of the interstitial layer may lead to fluorescence quenching due to the close proximity of the dye to the metal core or metal encapsulating layer. To achieve this placement of the fluorescent dye, the fluorescent dye may be added to the particles a period of time after the process for vowing the interstitial layer on the core has been initiated. In this way, there will be no dye close to the core metal and the majority of the dye may be incorporated towards the middle of the interstitial layer. In one or more embodiments, a fluorescent dye may be added between 1 and 5 hours after the growth of the interstitial layer on the core has been initiated.

Figure 9:
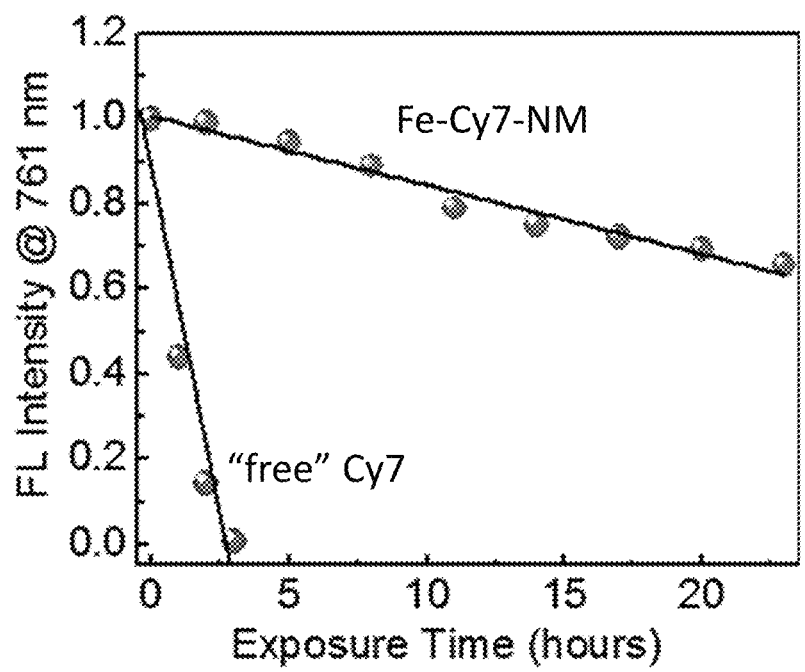
FIG. 9 shows a plot of fluorescence intensity versus exposure time for phosphate buffered saline (PBS) solutions of similar concentrations of "free" Cy7 dye and Cy7 dye that is included in the interstitial layer of an iron containing NM particle.

FIG. 9 shows a plot of fluorescence intensity versus exposure time for phosphate buffered saline (PBS) solutions of similar concentrations of "free" Cy7 dye (e.g. simply dissolved Cy7 dye) and Cy7 dye that is included in the interstitial layer of an iron containing NM particle. The fluorescence intensity of the solutions was measured on a spectrofluorometer every hour over a period of 24 hours. The results suggest that ~100% of the "free" Cy7 dye photobleach within 3 hours with a rate of k=0.0275 min$^{-1}$ while only 50% of the Cy7 dye entrapped into the Fe-Cy7-NM system photobleach within 26 hours with a rate of k=0.000306 min$^{-1}$.

Figure 10:
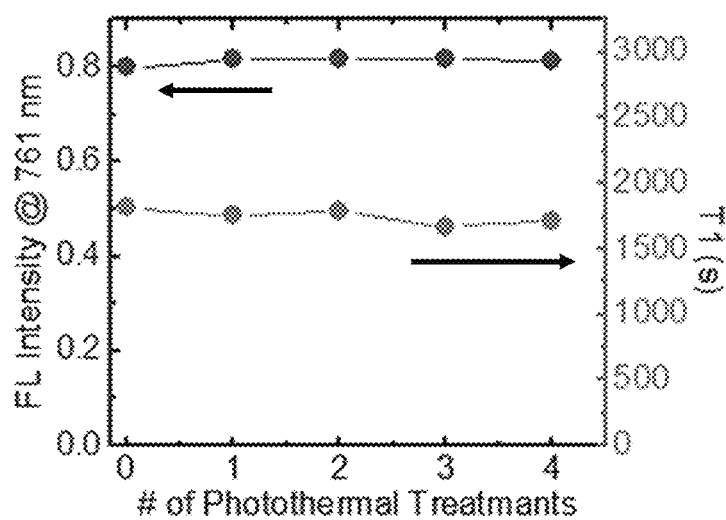
FIG. 10 shows a plot depicting the optical stability of the fluorescence intensity of the Fe-Cy7-NM (bottom) and the $T_1$ Longitudinal rate of Fe-Cy7-NM at 4.7 T and (top) versus the number of photo-thermal illumination cycles.

It is important to ensure long term stability of both the fluorescence and MRI imaging capabilities under realistic conditions such as photothermal heating. The T$_1$ relaxation time and fluorescence signal of Fe-Cy7-NM were measured and then irradiated at 1 W/cm$^2$ for 3 minutes so that the solutions reached a temperature of approximately 60° C., a temperature greater than in vivo temperatures for photothermal therapy. The solution were then cooled for 2 minutes. Multiple heating cycles were performed and the T$_1$ relaxation time and fluorescence signal were re-measured after each cooling period. FIG. 10 shows a plot depicting the optical stability of the fluorescence intensity of the Fe-Cy7-NM (bottom) and the T$_1$ Longitudinal rate of Fe-Cy7-NM at 4.7 T and (top) versus the number of photo-thermal illumination cycles. As shown in FIG. 10, little to no change in the T$_1$ relaxation time through 4 heating cycles was observed. Likewise, the fluorescence signal remained unchanged through these heating cycles. These stability results suggest that Fe-Cy7-NM should maintain its dual-imaging functionality upon laser irradiation, potentially enabling multiple rounds of laser treatment which could improve the outcome of such a therapy.

The particle including the interstitial layer around the core may be incubated with additional seed particles and a plating solution, as discussed above, to form the encapsulating layer around the interstitial layer. Forming the encapsulating layer in this manner may trap the MRI active material and/or the fluorescent material within the interstitial layer. Multifunctional fluorescent and MRI-active particles/nanostructures may be formed using different processes, repeating some of the above processes, incorporating additional processes, or omitting any of the above processes without departing from the invention.

In some embodiments of the invention, a functionalization layer may be disposed on an exterior surface of the encapsulating layer. The functionalization layer may modify the chemical reactivity of the particle/nanostructure for targeting and/or include additional drug payloads for therapeutic functions. In one or more embodiments of the invention, the exterior of the encapsulating layer may be functionalized with molecules including polyethyleneglycol (PEG), DNA/aptamers, proteins, polypeptides, antibodies, or other polymeric molecules.

While in the above discussion the particles/nanostructures have been described as having a core, an interstitial layer, and an encapsulating layer, embodiments of the invention are not limited to only one of each. Particles/nanostructures may incorporate as many interstitial layers and encapsulating layer as desired without departing from the invention. For example, multiple encapsulating and/or interstitial layers may be formed to modify a plasmon resonance frequency of the particles/nanostructures. In other words, the plasmon resonance may be tuned to a desired frequency through the use of multiple encapsulating and/or interstitial layers.

One or more embodiments of the invention may provide one or more of the following advantages: (i) A multifunctional fluorescent and MRI-active nanostructure in accordance with embodiments of the invention may reduce the toxicity of an MRI active material by encapsulating the MRI active material thereby limiting (or even eliminating) the direct exposure of the MRI active material to the surrounding environment, (ii) the multifunctional fluorescent and MRI-active nanostructures may provide an improved MRI contrast by incorporating MRI active materials within an encapsulating layer, and (iii) the multifunctional fluorescent and MRI-active nanostructures may be optically active and thereby enable optical tracking of the nanostructures and/or photo thermal therapy to be performed. In one or more embodiments, the multifunctional fluorescent and MRI-active nanostructures may be used for in vivo optical tracking of the nanostructures.

In one or more embodiments, the core may be a gold nanorod. The use of a gold nanorod may allow for tailoring the multifunctional fluorescent and MRI-active nanostructure may have a plasmon resonance that is tailored to the near-IR window of the electromagnetic spectrum (i.e., from about 700 nm to 2500 nm). In particular, the multifunctional particles of the present disclosure may have a plasmon resonance that peaks within the first water window regime (e.g., from about 700 nm to about 900 nm), where tissue is transparent and has a high light depth penetration. In one or more embodiments, the particles according to the present disclosure may have a plasmon resonance that peaks in a region between about 1000 nm and 1350 nm, which may provide for improved signal-to-noise ratios during in vivo imaging.

One or more embodiments, of this invention can be used for photothermal therapy due to the multifunctional particles strong near-IR Fano-resonant optical absorption properties. Passive tumor targeting systems rely on the enhanced permeability and retention effect for accumulation in the tumor. However, the ability to determine the anatomically precise location of theranostic nanoparticles in the body, in real time, before, during, and after treatment is a critically important. One or more embodiments of this invention could enable the monitoring of theranostic nanoparticles to enhance the efficacy of therapy. In one or more embodiments, an outer gold shell could also be functionalized with a drug payload and/or a targeting moiety for improved therapeutic function.

The ability for the chelated metals to interact with neighboring water molecules could enable medical imaging via $^1$H MRI in addition to particle tracking. This could enable the monitoring of a tumor before and after treatment. When fluorine containing molecules are included in the interstitial layer $^{19}$F-MRI can be used to image the particle as well and can be overlaid with the $^1$H MRI image for confirmation. By adding fluorescent dyes in the silica interstitial layer, the multifunctional particles may be capable of fluorescence imaging as well. Further, when dyes are included in the interstitial layer they show a significantly reduced photobleaching rate for the dye when compared to the free dye.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

What is claimed is:

1. A Magnetic Resonance Imaging (MRI) enhancement agent, comprising:
a plurality of particles, each particle comprising:
a metal core, wherein a radius of the metal core is between about 5 nm and 60 nm;
a dielectric shell disposed on the metal core, the dielectric shell comprising:
a dielectric material;
a fluorescing, phosphorescent, or luminescent material loaded in a middle portion of the dielectric shell along a thickness of the dielectric shell; and
at least one MRI contrast agent comprising a type 1 contrast agent, wherein the type 1 contrast agent is a chelated metal ion; and
a metal shell disposed on the exterior surface of the dielectric shell that encapsulates the dielectric shell, wherein the metal shell is the outermost layer of the particle.

2. The magnetic resonance imaging enhancement agent of claim 1, wherein the thickness of the dielectric shell is between about 5 and 40 nm.

3. The magnetic resonance imaging enhancement agent of claim 1, wherein a thickness of the metal shell is between 1 and 100 nm.

4. The magnetic resonance imaging enhancement agent of claim 1, wherein at least a portion of the plurality of particles supports a plasmon resonance centered at greater than 400 nm and less than 1200 nm.

5. The magnetic resonance imaging enhancement agent of claim 1, wherein the dielectric material is amorphous silica.

6. The magnetic resonance imaging enhancement agent of claim 1, wherein the at least one MRI contrast agent further comprises a type 2 contrast agent, wherein the type 2 contrast agent is iron oxide.

7. The magnetic resonance imaging enhancement agent of claim 1, wherein the chelate is selected from diethylene triamine pentaacetic acid or 2-(4-Isothiocyanatobenzyl)-1,4,7,10-tetraazacyclododecane-1,4,7,10 tetra acetic acid.

8. The magnetic resonance imaging enhancement agent of claim 1, wherein the metal core is gold or silver.

9. The magnetic resonance imaging enhancement agent of claim 1, wherein the metal shell is gold or silver.

10. The MRI enhancement agent of claim 1, wherein the at least one MRI contrast agent has a diameter of less than 5 nm.

11. A method of producing the particles of claim 1, comprising:
   coating the metal core with the dielectric material to obtain a dielectric coating around the metal core;
   loading the dielectric coating with the at least one MRI contrast agent and chemically bonding the chelated metal ion to the dielectric material to obtain the dielectric shell;
   seeding the exterior surface of the dielectric shell with a metal to obtain a seeded dielectric shell; and
   coating the seeded dielectric shell with a metal plating solution to obtain the metal shell that encapsulates the dielectric shell.

12. The method of claim 11, wherein the dielectric is amorphous silica.

13. The method of claim 12, wherein the amorphous silica is doped with an amine.

14. The method of claim 13, wherein the amine is 3-aminopropyl-triethoxysilane.

15. The method of claim 11, wherein the metal core is gold or silver.

16. The method of claim 11, wherein the metal seeded on the dielectric is gold or silver.

17. A Magnetic Resonance Imaging (MRI) enhancement agent, comprising:
   a plurality of particles, each particle comprising:
   a metal core, wherein a radius of the metal core is between about 5 nm and 60 nm;
   a dielectric shell disposed on the metal core, the dielectric shell comprising:
   a dielectric material,
   a fluorescing, phosphorescent, or luminescent material loaded in a middle portion of the dielectric shell along a thickness of the dielectric shell;
   at least one MRI contrast agent; and
   a chelate, wherein the at least one MRI contrast agent is chelated to the chelate; and
   a metal shell disposed on the exterior surface of the dielectric shell that encapsulates the dielectric shell, wherein the metal shell is the outermost layer of the particle.

18. A Magnetic Resonance Imaging (MRI) enhancement agent, comprising:
   a plurality of particles, each particle comprising:
   a metal core;
   a dielectric shell disposed on the metal core, the dielectric shell comprising:
   silica;
   at least one MRI contrast agent loaded in the silica, the at least one MRI contrast agent selected from a type 1 contrast agent, wherein the type 1 contrast agent is a chelated metal ion; and
   a fluorescing, phosphorescent, or luminescent material loaded in a middle portion of the dielectric shell along a thickness of the dielectric shell; and
   a metal shell disposed on the exterior surface of the dielectric shell that encapsulates the dielectric shell, wherein the metal shell is the outermost layer of the particle.

* * * * *